(12) United States Patent
Grodzki (10) Patent No.: US 10,012,715 B2
(45) Date of Patent: Jul. 3, 2018

(54) METHOD AND APPARATUS FOR RECORDING A MAGNETIC RESONANCE DATA SET

(71) Applicant: Siemens Aktiengesellschaft, Munich (DE)

(72) Inventor: David Grodzki, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 565 days.

(21) Appl. No.: 14/683,561

(22) Filed: Apr. 10, 2015

(65) Prior Publication Data

US 2015/0293198 A1 Oct. 15, 2015

(30) Foreign Application Priority Data

Apr. 10, 2014 (DE) .................. 10 2014 206 917

(51) Int. Cl.
*G01V 3/00* (2006.01)
*G01R 33/54* (2006.01)
(Continued)

(52) U.S. Cl.
CPC ............ *G01R 33/543* (2013.01); *A61B 5/055* (2013.01); *G01R 33/4818* (2013.01); *G01R 33/56518* (2013.01)

(58) Field of Classification Search
CPC ...... G01R 33/54; G01R 33/543; G01R 33/48; G01R 33/4818; G01R 33/481; G01R 33/4824; G01R 33/4835; G01R 33/4828; G01R 33/565; G01R 33/56518; G01R 33/56536; G01R 33/56572; G01R 33/5611; A61B 5/0555
(Continued)

(56) References Cited

U.S. PATENT DOCUMENTS 9,297,870 B2  3/2016  Van Den Brink
2002/0032376 A1*  3/2002  Miyazaki ............ A61B 5/0263
                                                       600/410
(Continued)

OTHER PUBLICATIONS

Meng et al., "A Single-Scan T2* Mapping Method Based on Two Gradient-Echo Images with Compensation for Macroscopic Field Inhomogeneity"; Magnetic Resonance in Medicine; vol. 60; pp. 1388-1395; (2008).
(Continued)

*Primary Examiner* — Thang Le
(74) *Attorney, Agent, or Firm* — Schiff Hardin LLP (57) ABSTRACT

In a method and apparatus for recording a magnetic resonance data set of a target region of an object, wherein the target region contains at least one interfering object with a susceptibility difference from the rest of the target region that influences the homogeneity of the basic magnetic field, in particular a metal object and/or an air inclusion, in addition to a first raw data set of the target region recorded without additional dephasing, at least one further raw data set of the target region is recorded that corresponds to a raw-data specific additional dephasing of the spins in the target region. For each image point of the magnetic resonance data set, the maximum value raw data of the corresponding image points of all raw data sets in spatial domain are selected as magnetic resonance data.

12 Claims, 3 Drawing Sheets

(51) Int. Cl.
*A61B 5/055* (2006.01)
*G01R 33/48* (2006.01)
*G01R 33/565* (2006.01)

(58) Field of Classification Search
USPC .................................................. 324/300–322
See application file for complete search history.

(56) References Cited

U.S. PATENT DOCUMENTS

| | | | |
|---|---|---|---|
| 2006/0106300 A1 | 5/2006 | Seppenwoolde et al. | |
| 2010/0148774 A1* | 6/2010 | Kamata | G01R 33/243 |
| | | | 324/309 |
| 2010/0253339 A1 | 10/2010 | Gross | |
| 2011/0215804 A1 | 9/2011 | Deimling et al. | |
| 2012/0074940 A1* | 3/2012 | Kimura | A61B 5/055 |
| | | | 324/314 |
| 2012/0268121 A1 | 10/2012 | Hernando et al. | |
| 2013/0057281 A1 | 3/2013 | Feiweier | |
| 2013/0076356 A1 | 3/2013 | Jellus et al. | |
| 2013/0154641 A1* | 6/2013 | Grodzki | G01R 33/56572 |
| | | | 324/309 |
| 2013/0214785 A1* | 8/2013 | Shirai | A61B 5/055 |
| | | | 324/322 |
| 2014/0210471 A1* | 7/2014 | Stemmer | G01R 33/56554 |
| | | | 324/309 |

OTHER PUBLICATIONS

Franconi et al; "Susceptibility gradient quantization by MRI signal response mapping (SIRMA) to dephaser"; The International Journal of Medical Research and Practice; vol. 37; pp. 877-884; (2010).

Seppenwoolde et al: "Passive Tracking Exploiting Local Signal Conservation: The White Marker Phenomenon", Magnetic Resonance in Medicine vol. 50:pp. 784-790 (2003).

* cited by examiner

METHOD AND APPARATUS FOR RECORDING A MAGNETIC RESONANCE DATA SET

BACKGROUND OF THE INVENTION

Field of the Invention

The invention relates to a method for recording (acquiring) a magnetic resonance data set of a target region of an object with a magnetic resonance scanner, wherein the target region contains at least one interfering object with a susceptibility difference from the rest of the target region that influences the homogeneity of the basic magnetic field, in particular a metal object and/or an air inclusion. The invention also relates to a magnetic resonance apparatus for implementing such a method.

Description of the Prior Art

Magnetic resonance imaging is widely known and is in frequently used in clinical medical diagnosis. A basic field (B0 field) generated in the magnetic resonance scanner is as homogenous as possible in the imaging volume, and is used to align nuclear spins in a target region of a subject. Radio-frequency excitation (B1 field) excites the spins and the decay of the excitation is measured (detected) as a magnetic resonance signal. Usually, spatial resolution is obtained by means of gradient fields generated by a gradient coil arrangement, for example slice-selection gradients when radiating the radio-frequency excitation, phase-encoding gradients, and readout gradients. In order to obtain the best possible imaging quality, homogeneity of the B0 field and linearity of the gradient fields are required.

In this context, problems are caused by susceptibility differences in the target region which can form at the interfaces of objects in the target region, for example in the case of air inclusions and/or in the environment of metal, for example in the case of implants, prostheses, dental fillings and the like. The susceptibility differences disrupt the homogeneity of the basic field, which can in turn result in artifacts in the magnetic resonance image. Such artifacts depending on the magnetic resonance sequence used are identifiable from signal loss and/or distortion in the magnetic resonance image.

Methods have been suggested to reduce artifacts of this kind in magnetic resonance data sets, in particular in turbo-spin-echo (TSE)-based magnetic resonance sequences. Examples of these are methods such as WARP or SEMAT. A further method, which can be advantageous for imaging in the environment of disruptive objects, in particular metal objects, is the use of single-point imaging methods (SPI), for example as a RASP or SPRITE magnetic resonance sequence.

Since these magnetic resonance sequences read each k-space point at the same time, the dephasings induced by the susceptibility differences are the same at each point so that no distortion can occur in the image.

To date, no suitable solution for gradient-recalled-echo (GRE)-based magnetic resonance sequences, which enable shorter echo and repetition times than TSE-based magnetic resonance sequences, is known. In particular, due to the high T2* decay and the signal loss resulting therefrom, GRE sequences have been considered as unsuitable for imaging in the environment of objects, in particular metal objects.

An article by Jan-Henry Seppenwoolde et al., "Passive Tracking Exploiting Local Signal Conservation: The White Marker Phenomenon", Magnetic Resonance in Medicine 50:784-790 (2003) suggests a novel approach to passive tracking of paramagnetic markers during endovascular interventions. The concept of this is to enable a positive contrast in the environment of small paramagnetic markers by selective dephasing of resonant unperturbed spins and simultaneous rephasing of magnetically perturbed spins. This should make it easier to locate the paramagnetic markers. The Seppenwoolde et al. method does not provide any advantages for normal clinical imaging.

SUMMARY OF THE INVENTION

An object of the invention is to reduce or prevent dephasing-induced signal loss due to susceptibility differences at the interfaces of interfering objects, in particular with GRE sequences.

This object is achieved by a method of the type described in the introduction wherein, in accordance with the invention, in addition to a first raw data set of the target region recorded without additional dephasing, at least one further raw data set of the target region is recorded that corresponds to a raw-data specific additional dephasing of the spins in the target region. In accordance with the invention, for each image point of the magnetic resonance data set, the maximum value raw data of the corresponding image points of all raw data sets in the spatial domain are selected as magnetic resonance data.

It is preferable that such multiple further raw data sets be determined, in order to detect possible dephasings as extensively as possible. Therefore, the invention is a method with which rephasing of all spins in a specific frequency range, in particular the frequency range excited by the radio-frequency excitation can be achieved and hence the signal loss reduced or completely avoided. Therefore, a method of this kind can also be referred to as "rephased MRI". It is suggested that at least one further raw data set be recorded with which, in at least one direction, preferably the direction of the readout gradient, in addition to a conventional raw data set, that is the first raw data set, there is a dephasing unequal to zero. Therefore, there are at least two, preferably more than two, raw data sets, which can be reconstructed and compared in the image space pixel-by-pixel in order to select the raw data with the higher absolute value for the final resulting magnetic resonance data set, which is a merger of the raw data sets. In this way, it is possible for dephasings, which were induced by the gradient fields of the magnetic interference, that is the interference fields, to be compensated again in the further raw data sets and hence for artifacts to be avoided to a large extent.

In other words, in addition to the conventional magnetic resonance image, the first raw data set, further images, the further raw data sets, with additional dephasing in at least one spatial direction, preferably the read-out direction, are recorded or determined. In each of the further raw data sets, according to the additional dephasing, the undesired dephasings induced by the susceptibility differences of at least a part of the spins are compensated; therefore, rephasing takes place. While therefore, in the first raw data set, these spins are dephased by the interference field and would only supply a reduced signal or no signal, this does not apply to at least one of the further raw data sets.

Following the reconstruction of the at least two raw data sets, they are compared in the image space image-point-by-image-point. In unperturbed regions, that is outside the influence of the interference field, the first raw data set will supply the highest raw data since the unperturbed spins in all other raw data sets are dephased by the additional dephasing. Depending upon the strength of the interference field, an image point in the region of the interference field will then show the highest signal when the dephasing of the further raw data set compensates the dephasing due to the interference field to an optimum degree. Therefore, in the image-point-by-image-point comparison, the dephasing stage with the highest absolute signal (raw data) is always selected image-point-by-image-point for a further merged image, in the final magnetic resonance data set, since then also the greatest number of spins are in phase (rephased). Therefore, in the merged magnetic resonance data set, image regions in the vicinity of a disruption that were dark in the first raw data set will now also supply a signal. Optimally, this will result in the formation of a magnetic resonance data set that no longer has any dephasing-induced signal losses or at least only has greatly reduced dephasing-induced signal losses.

As mentioned, it is most expedient for multiple further raw data sets to be recorded that all have a certain additional dephasing, which can, for example, be increased in steps. For example, it is conceivable for two to ten additional raw data sets to be determined; the higher the number of dephasing steps, that is of further raw data sets, the greater the likelihood of finding all perturbed spins rephased in at least one further raw data set. However, an increase in the recording time and/or the calculation time can be linked to an excessive number of further raw data sets.

It is noted again that rephasing gradients are in principle known in the prior art. If, for example, a gradient is applied at the time point of the radio-frequency excitation, it is possible to generate an additional phase for unperturbed spins which is compensated by a rephasing gradient such that the unperturbed spins are back in phase at the echo time. The invention relates to additional phases generated by interference fields and suggests the introduction of additional dephasing which again compensates this additional phase such that the correspondingly perturbed spins in the further raw data set are back in phase at the echo time. This has the inevitable result that, in the further raw data sets, in an implementation in which additional dephasing gradients are used, all unperturbed spins are dephased at the echo time. Therefore, in the further raw data sets, spins influenced by the interference field provide a higher signal contribution than unperturbed spins.

As mentioned, the method according to the invention was primarily developed for use with GRE sequences so that preferably a GRE sequence is used as the magnetic resonance sequence. However, it is can also be used with other magnetic resonance sequences, for example TSE sequences. It is also noted at this point that, when the interference field is greater than the maximum gradient strength of the magnetic resonance device, rephasing with GRE methods is no longer possible. Then, the spin can be inverted by a radio-frequency pulse, as is known from the TSE sequence, wherein then a GRE sequence as such would no longer be present but rather a SE sequence. Due to the long measuring time, however, this will probably be rarely used in practice.

There are two basic variants for determining the further raw data sets. In a first, less preferred embodiment, the raw data sets are recorded in different recording processes, in particular in each case after inherent radio-frequency excitation, wherein for the recording of the further raw data sets in each case different dephasing gradients are switched in at least one direction in the target region, in particular in the read-out direction and/or slice-selection direction. Therefore, in this embodiment of the invention, the magnetic resonance sequence used is modified by, in at least one direction, generally the read-out direction, a dephasing gradient corresponding to the additional dephasing is switched.

However, it is then necessary to provide an inherent recording process for each further raw data set, which can prolong the overall recording time.

Therefore, in a more preferred variant of the present invention, the raw data sets are at least partially recorded in one single recording process, and the data are entered into k-space that is enlarged compared to the recording of a single raw data set, and the raw data sets are determined from different regions of k-space with, in each case, in at least one direction in which k-space being enlarged, a displaced k-space center. This embodiment of the present invention is based on the knowledge that the dephasing provided for the further raw data sets in k-space corresponds to a displacement of the k-space. This means that, in the sphere of influence of an interference, the additional interference phase results in a displacement of k-space center. Here, the known formula for k-space (without interference)

$$\vec{k}(t) = \gamma \int_0^t \vec{G}(t')dt'$$

with the interference gradient field $G_{Int}$ becomes $$\vec{k}(t) = \gamma \int_0^t (\vec{G}(t') + \vec{G}_{Int})dt'.$$

In the context of the present invention, this relationship can be exploited by extending k-space that is to be filled, the extending being in at least one direction, preferably in the read-out direction. In the read-out direction, this is simple to achieve by the readout line in the k-space being extended due to the extension of the measuring period with the readout gradients, and therefore also is started earlier so that the center of k-space for the first raw data set is measured at the desired echo time. Thus the enlargement of k-space takes place in the readout direction, in particular by the extension of the readout period when a readout gradient is applied. Portions of this preferably symmetrically extended measured k-space, which was recorded in a single recording process, can then in each case be used for the reconstruction of a raw data set without this resulting in any notable extension of the measuring time since there is anyway some "free space" around the readout time window. In this case, the first raw data set is obviously formed such that the portion of k-space (which is the size of k-space that is normally to be recorded without the extension) around the actual k-space center is used. Therefore, a displacement of the k-space center in the readout direction also displaces this whole portion, wherein each displacement corresponds to a specific dephasing, and in this way, because the portion is displaced like a mask over the extended measured k-space, further raw data sets with specific dephasings can be determined. Thus, many different dephasing steps can be measured in one single recording process.

In an embodiment of the method according to the invention, an interference field map is determined in that, for each image point, an interference field value is determined from the dephasing value for which the maximum value raw data is present. The raw data determined can, therefore, also be used to create a field gradient map of the interference field, the interference field map. To this end, the dephasing steps for which raw data sets are available can be converted into gradient strengths to which they correspond as dephasing. In the image-point-by-image point comparison, the gradient strength or dephasing stage, in which the image point has the maximum value raw data is then assigned to each image point. In this case the spectral resolution of the interference field map again increases with the number raw data sets present so that a higher number of raw data sets are advantageous for this purpose as well. Obviously the echo time is necessary for the determination of the interference field or the interference field gradient so that the known relationship can be used.

The interference field map determined in this way can be used further in a variety of ways. For example, the interference field map can be used to prepare a subsequent measurement of the target region with the magnetic resonance device. Therefore, the recording of the magnetic resonance data set with the method according to the invention can be, for example, a type of scout scan, which is used to prepare a further measurement with the magnetic resonance device, with which the interference field map can then be used, for example, to enable active shimming in the target region. It is furthermore conceivable for the interference field map to be used in the context of a signal-separation technique for protons bound in different compounds. For example, if a Dixon technique is to be applied to the magnetic resonance data set, protons bound in water and in fat can be distinguished more effectively with reference to the interference field map. Other applications of the interference field map are also conceivable.

The procedure described so far can be used only to re-establish, by rephasing, the magnetic resonance signals of the spins that were actually excited. If therefore, the interference field did not excite any spins at all, signal loss is retained. Therefore, in a preferred embodiment of the invention, at least one further raw data set is acquired using a changed (different) excitation frequency for the radio-frequency excitation. This procedure is particularly expedient if the excitation is not intended to be slice selective, and therefore no slice selection gradient is applied. However, it is also conceivable for the shift of the excitation frequency (center frequency of the excited frequency band) to be set so strongly that, in the case of excitation in different slices, the slice excited by the changed excitation frequency lies far outside the slice stack actually to be measured, so that assignment problems are clearly avoided. If adjacent slices are also excited, it would be necessary to use a method that extracts the signals/raw data assigned to the slice actually to be measured.

When the method according to the invention is used over the entire target region, so that the highest signal value of all raw data sets is always used for each image point in the image space, there may be an amplification of the noise in regions outside the object to be recorded or regions that provide only a few signals, such as in air-filled regions, since then the highest signal value is always used and therefore the noise is accentuated. Therefore, in an embodiment of the invention, regions in the raw data sets belonging to the object are segmented and, for regions lying outside the object, the raw data of the first raw data set is always selected. Segmentation techniques are already extensively known in the prior art so that it is easily possible to define a mask within which the maximum value raw data is always selected for each image point. Outside the mask, the raw data of the first raw data set are used as a magnetic resonance data set so that the accentuation of the noise is avoided.

In addition to the method, the present invention concerns a magnetic resonance apparatus with a control computer designed to execute the method according to the invention.

All explanations with respect to the method according to the invention are applicable to the magnetic resonance apparatus according to the invention, with which it is also possible to achieve the aforementioned advantages of the present invention. The control computer therefore has a sequencer with which the other components of the magnetic resonance apparatus, such as gradient coils and radio-frequency coils, can be controlled for the implementation of a magnetic resonance sequence and for acquiring data. Furthermore, a reconstruction computer is provided for the determination of the magnetic resonance image data set from the raw data sets.

DESCRIPTION OF THE PREFERRED EMBODIMENTS

The basis of the present invention is to sample a further degree of freedom during the recording of magnetic resonance data, namely the dephasing. This enables spins that are subjected to a specific interference field or interference field gradient, which in turn brings about dephasing, nevertheless to make a contribution to the image. This principle is explained in more detail by the simple example in the article by Seppenwoolde et al. mentioned in the introduction, although this is not applicable to general magnetic resonance imaging. This is an attempt to depict the dephasing in the environment of a magnetic marker that causes interference of the B0 fields as lighter than the surrounding unperturbed tissue. In a conventional measurement with a GRE sequence, the magnetic resonance signal in the region of the interference would appear darker than the unperturbed tissue since the interference field Δ B(x,y,z) causes it to experience an additional phase, that is to say dephasing. The additional phase can be determined as $$\Phi_{Int} = \gamma \Delta B(x,y,z) TE.$$

Figure 1:
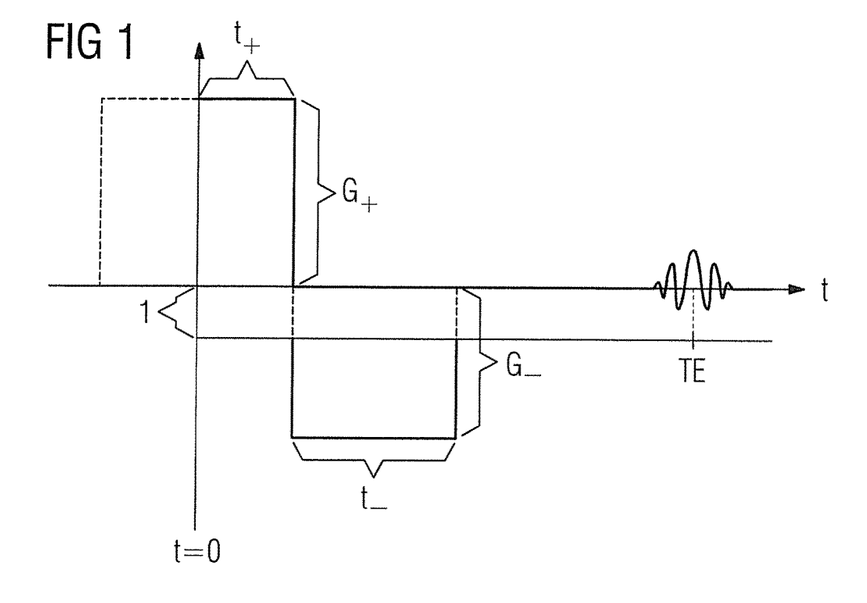
FIG. 1 is an illustration to explain the principles of the method according to the invention.

This is shown schematically in FIG. 1 for the slice selection. Here, the gradient is plotted against time. The radio-frequency excitation takes place at the time t=0. In this case, due to the slice-selection gradients or the gradient moment thereof G+t+, spins obtain an additional phase, which has to be rephased by the gradient moment G−t−. However, however due to the interference field 1 present from the time point t=0 of the radio-frequency excitation until the echo time, an additional phase is present which results in the dephasing of the spins.

The procedure described in the Seppenwoolde et al. article then attempts to use additional gradients (moments) to compensate this dephasing again so that the perturbed spins are back in phase at the echo time TE. The inevitable result of this is that all unperturbed spins are dephased by the additional gradient moment at the echo time TE. Therefore, in the Seppenwoolde et al. method, perturbed spins provide a higher signal contribution than unperturbed spins. Since the magnetic markers are generally much smaller than the image resolution, the interference field is effective only in the environment of one or fewer image points. It is therefore in accordance with the invention to select a consistent pretested dephasing stage by an additionally applied dephasing gradient.

However, the object of the method according to the invention is to generate a magnetic resonance data set in which the dephasing that occurs due to magnetic interference is compensated so that ideally the magnetic resonance data of each image point are rephased and depicted with the amplitude that would be present without interference. Interference fields that occur in practice, which are triggered by metal objects or air inclusions, have a much greater extension than the markers/tracers used by Seppenwoolde et al. and also have a more complex structure. It is, therefore, suggested that, in addition to conventional magnetic resonance recording, the first raw data set, with which no additional dephasing is used, further raw data sets, in particular at least three further raw data sets, be recorded or determined for the same target region with different dephasing steps. In this way, depending upon the dephasing stage, the image points in the raw data set that were negatively subjected to the same dephasing due to the interference, are rephased again. In mathematical terms, this means that the dephasing phase must be $\Phi_{Dephase}=-\Phi_{Int}$.

Figure 2:
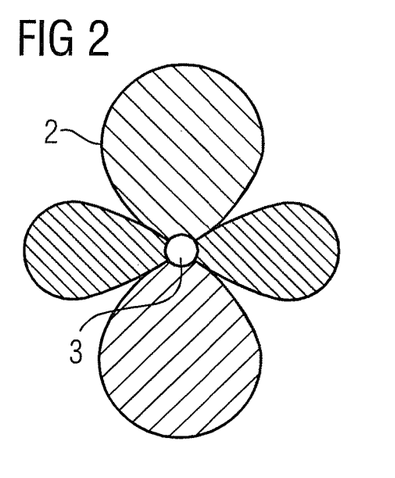
FIG. 2 shows a possible configuration of an interference field.
Figure 3:
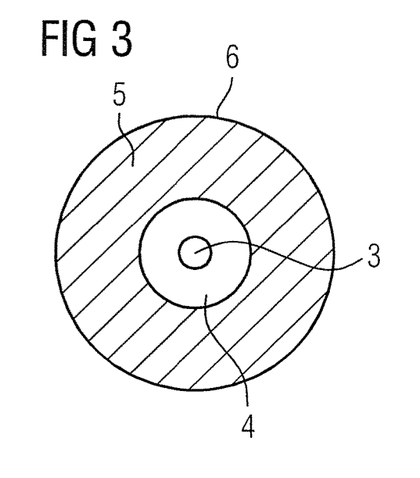
FIG. 3 illustrates a first raw data set with the interference field according to FIG. 2.
Figure 4:
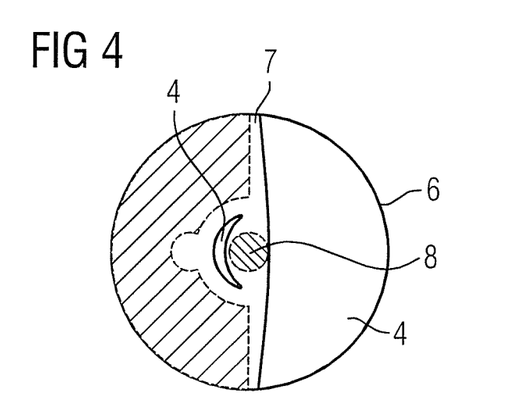
FIG. 4 illustrates a further raw data set with an interference field according to FIG. 2.

FIGS. 2 to 4 explain this in more detail. FIG. 2 is a schematic diagram of a map of the magnetic interference field 2 such as that created by a metal ball 3 as an interfering object with a strong susceptibility difference from the rest of the target region, for example tissue. The result of this interference field 2 is now (see FIG. 3) that, during a recording of a magnetic resonance image without additional dephasing in a region 4 around the metal ball 3 indicated by dashed lines, a signal extinction occurs due to the dephasing of the spins, while outside the region 4 the unperturbed spins in a unperturbed region 5 supply their usual magnetic resonance signal. Therefore, in the end, the schematically depicted magnetic resonance image in FIG. 3 corresponds to an example of a first raw data set, since there is no additional dephasing here. At the same time, incidentally, the outer interfaces 6 of the region 5 also form the outer interfaces of an object in which, in the present exemplary model, the metal ball 3 is embedded.

FIG. 4 shows schematically what changes occur compared to the magnetic resonance image in FIG. 3 on the introduction of additional dephasing. It can be seen that such a magnetic resonance image corresponding to a further raw data set also includes regions 5 in which signal extinction is present since unperturbed spins are dephased too strongly. There are also regions 7 with a weak magnetic resonance signal. However, it can be seen that a region 8 in which previously no magnetic resonance signal was received now contains higher value raw data; this means that perturbed spins in this region were brought back into phase by the additional dephasing at the echo time and so they can be measured.

If now, in addition to the further raw data set shown in FIG. 4, further raw data sets with other dephasing steps are recorded, a good part of the data from the extinction region 4 is obtained for a merged magnetic resonance data set in which the highest value raw data is always used for each image point. It may be assumed that the interference could be most effectively compensated in the dephasing stage with the highest value raw data and therefore the magnetic resonance signal obtained is closest to the raw data that would exist without interference.

Figure 5:
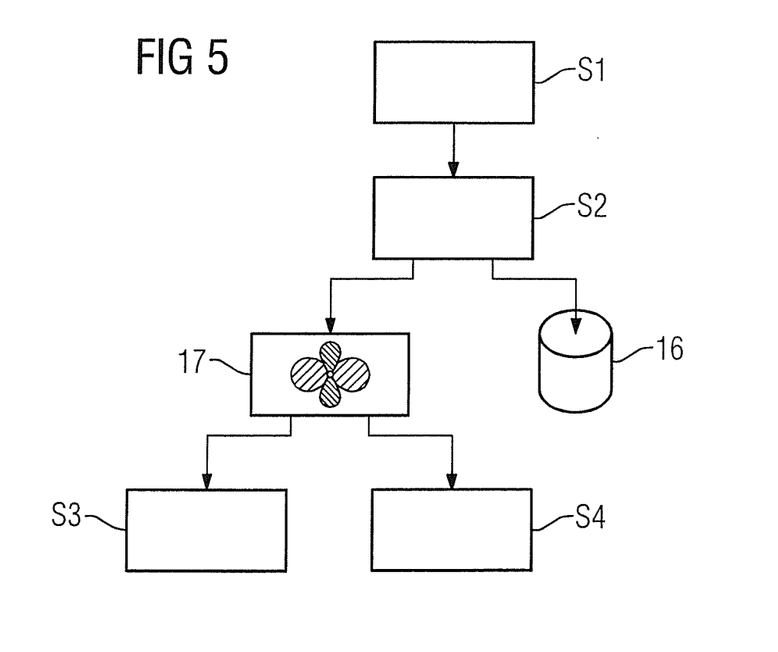
FIG. 5 is a flowchart of an exemplary embodiment of the method according to the invention.

FIG. 5 shows a flowchart of an exemplary embodiment of the method according to the invention. Here, the raw data sets are recorded in a step S1. In the present case, this takes place by all dephasing steps being executed in a single recording process. This makes use of the fact that the dephasing corresponds to a displacement in the k-space, as is expressed in greater detail by the formulas shown above. This will be explained in more detail with respect to FIG. 6. This shows that the entirety of k-space 9 is sampled in step S1, which is extended in the readout direction 11 compared to the usual k-space 10 shown as hatched, which was selected for a recording without additional dephasing. It should be noted that, in the present case, it is assumed that the magnetic resonance data set is a desired absolute value magnetic resonance data set for which phase effects cancel each other out in the phase-encoding direction without further artifacts. If phase images are involved or if another gradient structure is used during the recording, obviously dephasing and extension of k-space in directions other than the readout direction 11 are in principle conceivable.

Figure 6:
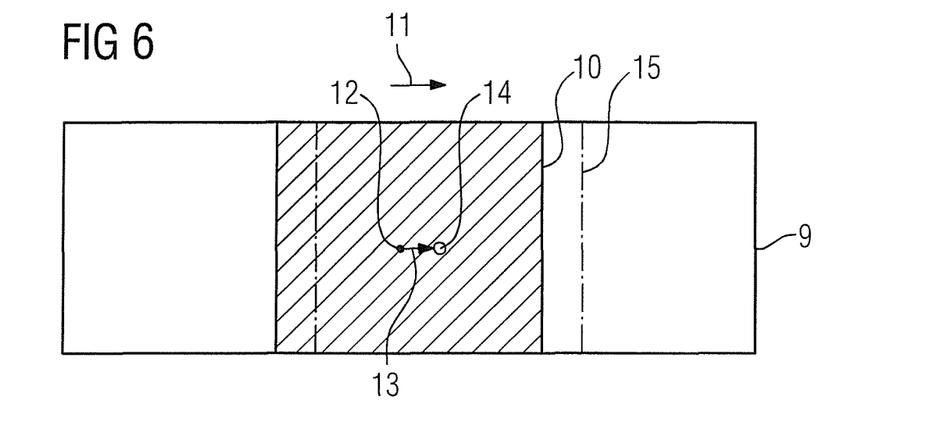
FIG. 6 shows extended k-space and reconstruction regions for raw data sets.

The center 12 of extended, sampled k-space 9 also corresponds to the center of k-space 10, which therefore forms a central portion from which the first raw data set is reconstructed. Therefore, to sample extended k-space 9, the readout time window is extended symmetrically.

If the center 12 of k-space 9 is now displaced (shifted) to a new position 14, for example as shown by the arrow 13 and the portion described by k-space 10 is displaced together with this, a new reconstruction base for a further raw data set is obtained, the limits 15 of which are also shown in FIG. 6. This means that the limits 15 define the portion around the position 14 as the center of this portion from which a further raw data set is determined. Due to the displacement according to the arrow 13 in the readout direction 11, this corresponds to dephasing in the readout direction; in this context, see once again the formulas mentioned above.

As can be seen from FIG. 6, this enables the definition of numerous portions within extended k-space 9, wherein, on displacement in the direction opposite to the arrow 13, these portions also in each case correspond to specific additional dephasings in the readout direction 11, that is dephasing steps. Thus, numerous, preferably all, raw data sets in step S1 can be recorded in a single recording process following a single excitation.

In the present case, the measurement of extended k-space itself takes place with a magnetic resonance sequence embodied as a GRE sequence.

In a step S2 (see FIG. 5 once again) it is optionally possible first to use segmentation to determine a mask which removes the regions lying outside the object to be recorded from further consideration; for these image points, the raw data of the first raw data set are used as magnetic resonance data in order avoid any change to the noise portion there to the greatest degree possible. In the step S2, the values of the raw data are compared for the image points assigned as masked for the object. The highest value raw data is used as magnetic resonance data in the magnetic resonance data set 16 depicting a result of the method. However, the dephasing stage, that is ultimately the raw data set from which this highest value raw data was removed, is also stored.

With knowledge of the echo time, it is possible to use the above relationship with the dephasing to calculate a value for the interference field which can be used in an interference field map 17. The interference field map 17 can be further used in different ways, for example in the step S3 to improve shimming measures for subsequent imaging or in step S4 to improve a separation technique for protons bound in different materials, for example a Dixon technique for separating protons bound in fat and water.

Figure 7:
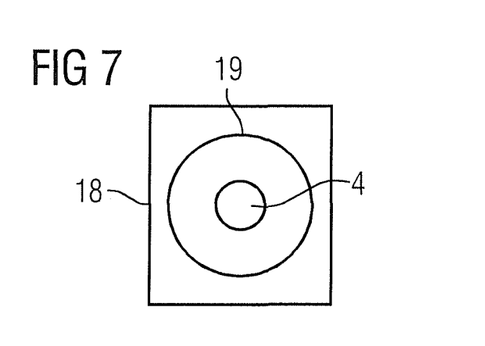
FIG. 7 illustrates a first raw data set.
Figure 8:
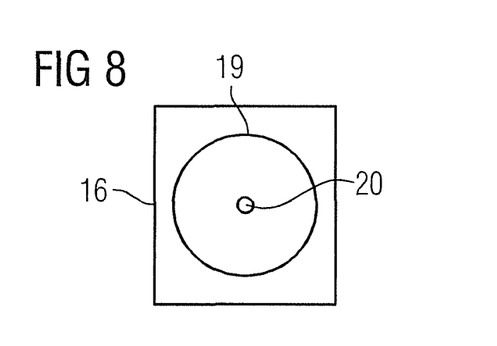
FIG. 8 illustrates a magnetic resonance data set of a region corresponding to that in FIG. 7 resulting with the method according to the invention.

FIG. 7 and FIG. 8 are schematic diagrams of the improvements that can be achieved with the method according to the invention. FIG. 7 shows a first raw data set 18, which ultimately corresponds to a magnetic resonance data set recorded in the conventional way. It can be seen that once again the object 19 includes the extinction region 4 in which no signal is obtained due to the dephasing.

FIG. 8 is a schematic diagram of a magnetic resonance data set 16 of the same target region obtained with the method according to FIG. 5. In this case, magnetic resonance data, i.e. image signals, are present in the entire object 19, wherein the interfering object 20 triggering the interference field is actually identifiable.

Figure 9:
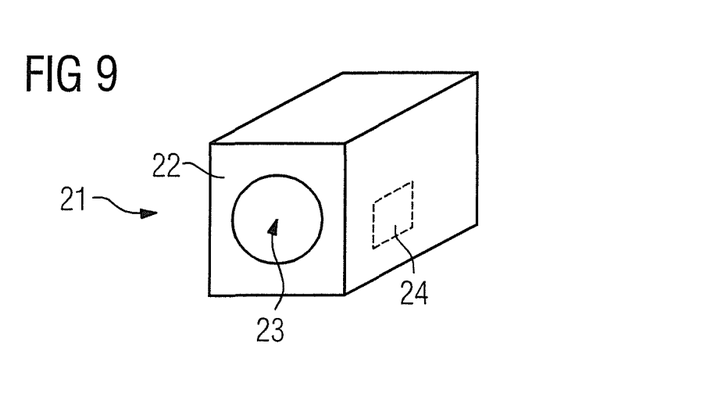
FIG. 9 schematically illustrates a magnetic resonance device according to the invention.

FIG. 9 is a schematic illustration of a magnetic resonance apparatus 21 according to the invention. As is known, this has a basic magnetic unit scanner defining a patient accommodation 23, which, not shown for clarity, can be surrounded by a gradient coil arrangement and a high-frequency coil arrangement. It is also possible to use local coils in the context of the present invention. The operation of the magnetic resonance apparatus 21 and the components thereof is controlled by a control computer 24, which is configured to cause the method according to the invention to be implemented. To this end, the control computer 24 can have a sequencer, which controls the acquisition of magnetic resonance data or raw data, and furthermore a reconstruction computer in order to calculate the magnetic resonance data set according to the method according to the invention from different raw data sets.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for acquiring magnetic resonance (MR) data from a target region of an examination object, comprising:
   from a control computer, operating an MR scanner, while the examination object is situated in a basic magnetic field that is produced by the MR scanner the MR scanner, to acquire a first raw MR data set and at least one further raw MR data set produced by excited nuclear spins in said target region, said target region containing at least one interfering object that has a magnetic susceptibility that differs from a remainder of said target region, which produces an interference field that degrades a homogeneity of said basic magnetic field, and thereby causes a dephasing of said nuclear spins;
   from said control computer, operating said MR scanner to acquire said first MR raw data set with no dephasing other than the dephasing produced by said interference field, and to acquire said at least one further raw MR data set with additional dephasing of said nuclear spins;
   from said control computer, entering raw data from said first raw MR data set and said at least one further raw MR data set into an electronic memory organized as k-space, comprising a plurality of k-space points, with each k-space point having a raw data value produced by the raw data entered thereat;
   from said control computer, generating a magnetic resonance data set, comprising image points, with each image point in said magnetic resonance data set having a value that is the highest value, among the raw data values for the corresponding k-space point among the first raw MR data set and the at least one further raw MR data set; and
   from said control computer, making said magnetic resonance data set available in electronic form as a data file.

2. The method as claimed in claim 1 comprising, from said control computer, operating said MR scanner to acquire said first raw MR data set and said at least one further raw MR data set in respectively different acquisition procedures, each acquisition procedure including radio-frequency excitation of said nuclear spins and in each acquisition of said at least one further raw MR data set, and producing said additional dephasing by operating said MR scanner to apply respectively different dephasing gradients in at least one direction in said target region, selected from the group consisting of a readout direction and a slice-selection direction.

3. The method as claimed in claim 1 comprising, from said control computer, operating said MR scanner to acquire said first raw MR data set and said at least one further raw MR data set in a single acquisition procedure, and producing said additional dephasing by entering said first raw MR data set and said at least one further raw MR data set from said single acquisition procedure into k-space having a size that is enlarged in at least one direction with respect to a size of k-space needed for a single raw MR data set, with said first raw MR data set and said at least one further raw MR data set occupying respectively different regions in k-space, with each region being shifted in k-space, along said at least one direction, with respect to a center of k-space.

4. The method as claimed in claim 3 comprising, from said control computer, operating said MR scanner to acquire said first raw MR data set and said at least one further raw MR data set during application of a readout gradient in a readout direction, and wherein k-space is enlarged in said readout direction by extending a time duration during which said readout gradient is applied.

5. The method as claimed in claim 1 comprising, in said control computer, determining an interference field map of said interference field by, for each image point in said magnetic resonance data set, determining an interference field value from the dephasing value for said highest raw data value.

6. The method as claimed in claim 5 comprising, from said control computer, using said interference field map to prepare a subsequent acquisition of MR data from said target region with said MR scanner.

7. The method as claimed in claim 5 comprising, from said control computer, using said interference field map in a signal-separation technique for evaluating MR data acquired using said MR scanner from protons that are bound in different compounds.

8. The method as claimed in claim 1 comprising, from said control computer, operating said MR scanner to acquire at least one additional raw MR data set from said target region with said nuclear spins being excited at a different excitation frequency compared to acquisition of said first raw MR data set and said at least one further raw MR data set.

9. The method as claimed in claim 1 comprising, in said control computer, segmenting a region produced by said examination object in each of said first raw MR data set and said at least one further raw MR data set and generating said magnetic resonance image data set using only the raw data from said first raw MR data set for regions outside of said segmented examination object.

10. The method as claimed in claim 1 comprising, in said control computer, segmenting a region produced by said examination object in said magnetic resonance image data set and, for regions outside of said segmented examination object, using only raw data from said first raw MR data set.

11. The method as claimed in claim 1 comprising, from said control computer, operating said MR scanner using a GRE sequence to acquire said first raw MR data set and said at least one further raw MR data set.

12. A magnetic resonance (MR) apparatus comprising:
an MR scanner;
a control computer configured to operate said MR scanner, while an examination object is situated in a basic magnetic field produced by the MR scanner, to acquire a first raw MR data set and at least one further raw MR data set produced by excited nuclear spins in a target region of the examination object, said target region containing at least one interfering object that has a magnetic susceptibility that differs from a remainder of said target region, which produces an interference field that degrades a homogeneity of said basic magnetic field, and thereby causes a dephasing of said nuclear spins;
said control computer being configured to operate said MR scanner to acquire said first MR raw data set with no dephasing other than the dephasing produced by said interference field, and to acquire said at least one further raw MR data set with additional dephasing of said nuclear spins;
an electronic memory organized as k-space, comprising a plurality of k-space points;
said control computer, entering raw data from said first raw MR data set and said at least one further raw MR data set into said electronic memory, with each k-space point having a raw data value produced by the raw data entered thereat;
said control computer being configured to generate a magnetic resonance data set, comprising image points, with each image point in said magnetic resonance data set having a value that is the highest value among the raw data values for the corresponding k-space point among the first raw MR data set and the at least one further raw MR data set; and
said control computer being configured to make said magnetic resonance data set available in electronic form as a data file.

* * * * *